United States Patent
Yang et al.

(10) Patent No.: US 9,494,518 B2
(45) Date of Patent: Nov. 15, 2016

(54) MULTISCALE SPECTRAL NANOSCOPY

(71) Applicants: Haw Yang, Princeton Junction, NJ (US); Kevin Welsher, Plainsboro, NJ (US)

(72) Inventors: Haw Yang, Princeton Junction, NJ (US); Kevin Welsher, Plainsboro, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 14/415,779

(22) PCT Filed: Jul. 18, 2013

(86) PCT No.: PCT/US2013/051062
§ 371 (c)(1),
(2) Date: Jan. 20, 2015

(87) PCT Pub. No.: WO2014/015128
PCT Pub. Date: Jan. 23, 2014

(65) Prior Publication Data
US 2015/0177149 A1    Jun. 25, 2015

Related U.S. Application Data

(60) Provisional application No. 61/772,617, filed on Mar. 5, 2013, provisional application No. 61/672,837, filed on Jul. 18, 2012.

(51) Int. Cl.
*F21V 9/16* (2006.01)
*G01N 21/64* (2006.01)
(Continued)

(52) U.S. Cl.
CPC .......... *G01N 21/6458* (2013.01); *G01Q 90/00* (2013.01); *G02B 21/0024* (2013.01); *G01N 15/1475* (2013.01)

(58) Field of Classification Search
CPC ...................... G01N 21/6458; G01N 15/1475; G02B 21/0076; G02B 21/0024; G02B 21/361; G02B 21/0032; G02B 21/0036; G02B 21/0048; G02B 21/008; G02B 21/26; G02B 21/365; G01Q 90/00
USPC ....................................................... 250/459.1
See application file for complete search history.

(56) References Cited

U.S. PATENT DOCUMENTS 5,699,193 A   12/1997   Monno
6,317,258 B1 *   11/2001   Watanabe .......... G02B 21/0024
                                             359/202.1

(Continued)

OTHER PUBLICATIONS

Cang, H. et al. "Confocal Three Dimensional Tracking of a Single Nanoparticle with Concurrent Spectroscopic Readouts" Applied Physics Letters, vol. 88, (2006).
(Continued)

*Primary Examiner* — David J Makiya
*Assistant Examiner* — Taeho Jo
(74) *Attorney, Agent, or Firm* — Meagher Emanuel Laks Goldberg & Liao, LLP (57) ABSTRACT

A system and method for non-invasively tracking a particle in a sample is disclosed. The system includes a 2-photon or confocal laser scanning microscope (LSM) and a particle-holding device coupled to a stage with X-Y and Z position control. The system also includes a tracking module having a tracking excitation laser, X-Y and Z radiation-gathering components configured to detect deviations of the particle in an X-Y and Z directions. The system also includes a processor coupled to the X-Y and Z radiation gathering components, generate control signals configured to drive the stage X-Y and Z position controls to track the movement of the particle. The system may also include a synchronization module configured to generate LSM pixels stamped with stage position and a processing module configured to generate a 3D image showing the 3D trajectory of a particle using the LSM pixels stamped with stage position.

19 Claims, 9 Drawing Sheets

(51) Int. Cl.
G02B 21/00 (2006.01)
G01Q 90/00 (2010.01)
G01N 15/14 (2006.01)

(56) References Cited

U.S. PATENT DOCUMENTS

| | | | |
|---|---|---|---|
| 8,217,992 B2* | 7/2012 | Bewersdorf | G02B 21/0076 250/458.1 |
| 2003/0062484 A1* | 4/2003 | Nakata | G01J 3/06 250/458.1 |
| 2004/0217270 A1* | 11/2004 | Publicover | B82Y 35/00 250/234 |
| 2005/0200947 A1* | 9/2005 | Hirata | G02B 21/02 359/368 |
| 2006/0011832 A1* | 1/2006 | Wolleschensky | G02B 21/0072 250/310 |
| 2006/0012864 A1 | 1/2006 | Funk | |
| 2006/0013492 A1* | 1/2006 | Hecht | G06T 9/007 382/232 |
| 2007/0206846 A1* | 9/2007 | Cotton | G01R 31/311 382/144 |
| 2008/0075227 A1* | 3/2008 | Christoph | A61B 6/583 378/23 |
| 2008/0192231 A1* | 8/2008 | Jureller | G02B 21/008 356/36 |
| 2008/0285123 A1 | 11/2008 | Funk | |
| 2009/0262183 A1 | 10/2009 | Hayashi | |
| 2009/0263002 A1 | 10/2009 | Cremer et al. | |
| 2009/0296207 A1 | 12/2009 | Goelles | |
| 2009/0323058 A1* | 12/2009 | Dyba | G01N 21/65 356/301 |
| 2010/0213389 A1* | 8/2010 | Larkin | G01J 1/58 250/459.1 |
| 2010/0309304 A1* | 12/2010 | Chalmond | G02B 21/008 348/79 |
| 2011/0004447 A1 | 1/2011 | Hurley et al. | |
| 2011/0057121 A1* | 3/2011 | Yang | G01J 3/4406 250/491.1 |
| 2011/0211254 A1* | 9/2011 | Vizi | G02B 21/0048 359/385 |
| 2011/0220807 A1 | 9/2011 | Inoue | |
| 2011/0279667 A1* | 11/2011 | Vizi | G02B 21/0036 348/80 |
| 2011/0279893 A1* | 11/2011 | Vizi | G02B 21/002 359/380 |
| 2012/0038307 A1 | 2/2012 | Ahn et al. | |
| 2012/0135874 A1 | 5/2012 | Wang et al. | |
| 2012/0191163 A1* | 7/2012 | Yelin | A61K 47/48561 607/92 |
| 2012/0224034 A1* | 9/2012 | Kalkbrenner | G01N 21/6458 348/49 |
| 2012/0250000 A1* | 10/2012 | Lanzano | G01B 9/04 356/5.1 |
| 2013/0015370 A1* | 1/2013 | Damaskinos | G01N 21/6452 250/459.1 |
| 2013/0093873 A1* | 4/2013 | Bula | G02B 21/0048 348/79 |

OTHER PUBLICATIONS

Cang, H. et al, "Observation of Apectral Anisotropy of Gold Nanoparticles." Journal of Chemical Physics, vol. 129, (2008).
Xu, C. et al, "Rapid and Quantitative Sizing of Nanoparticles Using Three-Dimensional Single-Particle Tracking." Journal of Physical Chemistry C, vol. 111, pp. 32-35 (2007).
Ray, S. et al, "Kinesin Follows the Microtubule's Protofilament Axis." The Journal of Cell Biology, vol. 121, No. 5, pp. 1083-1093 (1993).
Snee, P. et al. "A Ratiometric CdSe/ZnS Nanocrystal pH Sensor" Journal of the American Chemical Society vol. 128, pp. 13320-13321, (2006).
Vlaskin, V. et al. "Tunable Dual Emission in Doped Semiconductor Nanocrystals" Nano Letters, vol. 10, pp. 3670-3674, (2010).
Li, S. et al. "Single Quantum Dots as Local Temperature Markers" Nano Letters, vol. 7, No. 10, pp. 3102-3105 (2007).
Hsia, C. et al. "An Accessible Approach to Preparing Water-Soluble Mn2+-Doped (CdSSe)ZnS (Core)Shell Nanocrystals for Ratiometric Temperature Sensing", ACS Nano, vol. 5, No. 12, pp. 9511-9522 (2011).
Frasco, M. et al. "Semiconductor Quantum Dots in Chemical Sensors and Biosensors" Sensors, vol. 9, pp. 7266-7286 (2009).
Forster, T. "Zwischenmolekulare Energiewanderung und Fluoreszenz" Annalen Der Physik 2, 55-75 (1948).
Hanson, J. et al. "Illuminating the Mechanistic Roles of Enzyme Conformational Dynamics." Proceedings of the National Academy of Sciences, vol. 104, No. 46, pp. 18055-18060 (Nov. 2007).
Watkins, L. et al. "Quantitative Single-Molecule Conformational Distributions: A Case Study with Poly-(1-proline)" Journal of Physical Chemistry A, vol. 110, pp. 5191-5203, (2006).
Flynn, E. et al. "Dynamic Active-Site Protection by the M. tuberculosis Protein Tyrosine Phosphatase PtpB Lid Domain." Journal of the American Chemical Society, vol. 132, pp. 4772-4780, (2010).
Ellis-Davies, G. Caged Compounds: Photorelease Technology for Control of Cellular Chemistry and Physiology. Nature Methods, vol. 4, No. 8, pp. 619-628, (2007).
Olejnik, J. et al. "Photocleavable Biotin Derivatives: a Versatile Approach for the Isolation of Biomolecules." Proceedings of the National Academy of Sciences, vol. 92, pp. 7590-7594 (1995).
Petran, M. et al. "Tandem-Scanning Reflected Light Microscope" Journal of the Optical Society of America, vol. 58, No. 5, pp. 661-664 (1968).
McAllister, R. et al. "Design and Optimization of a High-Speed, High-Sensitivity, Spinning Disk Confocal Microscopy System" Journal of Biomedical Optics, vol. 13, No. 5 (2008).
Wang, E. et al. "Performance Comparison Between the High-Speed Yokogawa Spinning Disc Confocal System and Single-Point Scanning Confocal Systems" Journal of Microscopy—Oxford, vol. 218, pp. 148-159 (2005).
Huisken, J. et al. "Optical Sectioning Deep Inside Live Embryos by Selective Plane Illumination Microscopy" Science, vol. 305, pp. 1007-1009 (2004).
Holekamp, T. et al. "Fast Three-Dimensional Fluorescence Imaging of Activity in Neural Populations by Objective-Coupled Planar Illumination Microscopy" Neuron, vol. 57, pp. 661-672, (2008).
Keller, P. et al. "Reconstruction of Zebrafish Early Embryonic Development by Scanned Light Sheet Microscopy" Science, vol. 322, pp. 1065-1069, (2008).
Keller, P. et al. "Fast, High-Contrast Imaging of Animal Development with Scanned Light Sheet-Based Structured-Illumination Microscopy" Nature Methods, vol. 7, No. 8, pp. 637-655 (2010).
Planchon, T. et al. "Rapid Three-Dimensional Isotropic Imaging of Living Cells Using Bessel Beam Plane Illumination" Nature Methods, vol. 8, No. 5, pp. 417-468 (2011).
Klar T. et al. "Fluorescence Microscopy with Diffraction Resolution Barrier Broken by Stimulated Emission" Proceedings of the National Academy of Sciences, vol. 97, No. 15, pp. 8206-8210 (2000).
Schmidt, R. et al. "Mitochondrial Cristae Revealed with Focused Light" Nano Letters, vol. 9, No. 6, pp. 2508-2510 (2009).
Rust, M. "Sub-Diffraction-Limit Imaging by Stochastic Optical Reconstruction Microscopy (STORM)." Nature Methods, vol. 3, No. 10, pp. 793-795 (2006).
Betzig, E. et al. "Imaging Intracellular Fluorescent Proteins at Nanometer Resolution" Science, vol. 313, pp. 1642-1645 (2006).
Juette, M. et al. "Three-Dimensional Sub-100 nm Resolution Fluorescence Microscopy of Thick Samples" Nature Methods, vol. 5, No. 6, pp. 527-529 (2008).
Shtengel, G. et al. "Interferometric Fluorescent Super-Resolution Microscopy Resolves 3D Cellular Ultrastructure" Proceedings of the National Academy of Sciences, vol. 106, No. 9, 3125-3130 (2009).
Thompson, M. et al. "Localizing and Tracking Single Nanoscale Emitters in Three Dimensions with High Spatiotemporal Resolution Using a Double-Helix Point Spread Function" Nano Letters, vol. 10, pp. 211-218 (2010).

(56) References Cited

OTHER PUBLICATIONS

Egners, A. et al. "Fast 100-nm Resolution Three-Dimensional Microscope Reveals Structural Plasticity of Mitochondria in Live Yeast" Proceedings of the National Academy of Sciences, vol. 99, pp. 3370-3375 (2002).

Gustafssoon, M. "Surpassing the Lateral Resolution Limit by a Factor of Two Using Structured Illumination Microscopy" Journal of Microscopy—Oxford, vol. 198, pp. 82-87 (2000).

Schermelleh, L. et al. "Subdiffraction Multicolor Imaging of the Nuclear Periphery with 3D Structured Illumination Microscopy" Science, vol. 320, pp. 1332-1336 (2008).

Shao, L. et al. "Super-Resolution 3D Microscopy of Live Whole Cells using Structured Illumination" Nature Methods, vol. 8, No. 12, (2011).

Cang, H. et al. "Guiding a Confocal Microscope by Single Fluorescent Nanoparticles" Optic Letters, vol. 32, No. 18, pp. 2729-2731, (2007).

* cited by examiner

MULTISCALE SPECTRAL NANOSCOPY

CROSS-REFERENCE TO PRIOR FILED APPLICATIONS

This application claims priority to U.S. provisional applications 61/672,837 which was filed on Jul. 18, 2012 and 61/772,617 which was filed on Mar. 5, 2013 which are both incorporated herein in their entirety.

GOVERNMENT RIGHTS IN THIS INVENTION

This invention was made with government support under Grant No. DE-SC0006838 awarded by the Department of Energy. The government has certain rights in this invention.

TECHNICAL FIELD

This invention relates generally to a systems and methods for tracking a single particle and more specifically, to systems and methods for imaging and analyzing single particles.

BACKGROUND

This disclosure pertains to Multiscale Spectral Nanoscopy (MSN) and is generally related to the disclosure in U.S. Pat. No. 7,982,194—Single Nanoparticle Tracking Spectroscopic Microscope (SNTSM) which is incorporated herein in its entirety. The study of molecular interactions in biological systems has long been hampered by the inability to observe molecular phenomena on their native length scale (down to <1 nm) and on a time scale relevant to molecular dynamics (<millisecond), while simultaneously placing these interactions and dynamics in their macromolecular biological context. The traditional methods of observing molecular biology in context have been optical imaging methods, starting with the most predominantly used and commercially available method: confocal microscopy.

Traditional Imaging Methods:

Modern day laser scanning confocal microscopes have the ability to provide optical sections at up to 8 Hz. Unfortunately, these speeds are not sufficient for the evaluation of biological processes which happen in real time in three dimensions. Confocal microscopes have been further improved by the implementation of Nipkow spinning disks, which allow the acquisition of 3D volumes at up to 1 Hz, with near confocal performance. However, these time scales (>1 second) are still far too slow to monitor chemical dynamics at the cellular or subcellular level.

Fast Large Scale 3D Imaging Methods:

To solve the problem of imaging large volumes with high temporal resolution selective plane illumination microscopy (SPIM) use an excitation beam that is spread out by a cylindrical lens and delivered to the sample perpendicular to the collection objective, creating a plane of illumination which allows for optical sectioning. Fast imaging of volumes of 400×400×200 um of neuronal action potentials every 6 seconds have been achieved, although the axial resolution is on the order of 5 microns. This method has been improved by rapidly scanning a laser beam to create an illumination plane, allowing for more intense illumination and faster acquisition times, acquiring volumes of 1000× 1000×600 um in 60-90 seconds with 300 nm lateral and 500 nm axial resolution.

Superresolution Methods:

While the above methods have opened doors to the study of larger dynamics in developmental biology, they are still limited by diffractive nature of propagating beams of light, with the ultimate resolution limit on the order of 200 nm in the lateral dimensions and 600 nm in the axial dimensions. To bypass this limit, so-called "super-resolution" methods have been developed. Stimulated emission depletion microscopy (STED) uses a high power laser pulse to effectively turn off fluorescence emission in a certain area. By carefully shaping the laser pulse to define a spherical area around the focal spot, the focal spot size can be effectively reduced in size due to the depletion of surrounding emission. Isotropic focal spots with resolution down to 30 nm have been used to image mitochondrial cristae in live cells. Unfortunately, this is still a point scanning technique and has limited time resolution at larger spatial scales.

Other methods have relied on localization of single photoswitchable fluorophores. These methods (stochastic optical reconstruction microscopy, STORM; photoactivated localization microscopy, PALM) were initially implemented for investigating phenomena in two dimensions, but have been extended to three dimensions for up to a few microns through the use of astigmatic imaging (STORM, 20-30 nm lateral, 60 nm axial), biplane imaging (BP-PALM, 30 nm lateral, 75 nm axial), interferometry (iPALM, 20 nm lateral, 10 nm axial), or implementing a double helix PSF (DH-PSF, 10 nm lateral, 10 nm axial). Unfortunately, all of these methods are limited by their axial extent (usually only 1-2 microns) or temporal resolution (PALM and STORM require the observation of many photoswitching events, requiring tens of seconds to acquire a single image).

Some methods have endeavored to combined fast 3D imaging with superresolution, such scanning multifocal multiphoton 4Pi-confocal microscopy (MMM-4Pi), in which a two photon excitation beam is broken into 16-64 beamlets which scan a small subsection of the optical slice. By stitching these subregions together and scanning axially through the specimen, volumes of 10×10×5 μm can be observed in as little as 150 seconds, with isotropic resolution from 100-140 nm. Another method which aims to combine the benefits of superresolution with larger scale observations is the structured illumination microscope (SIM). By implementing excitation fields with frequencies near the spatial frequencies of the sample, a lower beat frequency, observable by a traditional microscope objective, can be created. This method has shown the ability to improve the lateral resolution down to ~110 nm. This method has also been extended to three dimensions (3D-SIM) with volume imaging rates of 0.20 Hz for volumes of 25×25×2.72 um.

Despite these faster superresolution methods, there is still a huge range of length and time scales that go unobserved. For instance, the single-molecule methods such as DH-PSF and iPALM show remarkable spatial resolution, but they cover a relatively short length scale due to their small axial extent. Very few methods adequately address timescales below 1 msec. It would be desirable to provide systems and methods that address these and other shortcomings of existing systems.

SUMMARY OF THE INVENTION

A system and method for non-invasively tracking a particle in a sample is disclosed. The system includes a 2-photon or confocal laser scanning microscope (LSM) configured to scan the sample. The system also includes a particle-holding device with the particle coupled to the particle-holding device, the particle-holding device being coupled to a stage with X-Y and Z position control. The system also includes a tracking module having a tracking excitation laser, X-Y radiation-gathering components configured to detect deviations of the particle in an X-Y direction and Z radiation-gathering components configured to detect deviations of the particle in a Z direction. The system also includes a processor coupled to the X-Y and z radiation gathering components, generate control signals configured to drive the stage X-Y and Z position controls to track the movement of the particle.

The system may also include a synchronization module configured to receive current LSM scanning mirror positions and LSM detector readouts and synchronize them with current stage position to generate an LSM pixel stamped with stage position and a processing module configured to generate a 3D image showing the 3D trajectory of a particle using the LSM pixel stamped with stage position. The synchronization module may be configured to receive current LSM scanning mirror positions and LSM detector readouts and synchronize them with current stage position to generate an LSM pixel stamped with stage position. A pixel to voxel conversion module may be configured convert each detector readout (pixel) from the LSM system from lab frame to a three dimensional voxel in a sample frame based on known magnification of the LSM system (real space pixel size), and the piezoelectric stage position at each time point during the scan of the sample. An interpolation module may be configured to generate interpolated data including average oversampled voxels and interpolated unsampled voxels. A smoothing module may be configured to smooth the interpolated data. An image generating module may be configured to generate a 3D image showing movement of the particle based on the interpolated data.

The tracking excitation laser may be mounted parallel to an optical table plane and the X-Y radiation gathering components are mounted vertically with respect to the optical table plane. Each X-Y radiation gathering component may have a mirror configured to reflect light from the plane of the optical table to a vertical orientation. A vertical mounting surface may have X radiation gathering components mounted to one side and Y radiation gathering components mounted to an opposite side.

A method for non-invasively tracking a particle in a sample is also disclosed. The method includes providing a 2-photon or confocal laser scanning microscope (LSM) configured to scan the sample. The method also includes providing a particle-holding device with the particle coupled to the particle-holding device, the particle-holding device being coupled to a stage with X-Y and Z position control. The method also includes generating a tracking excitation laser beam and detecting deviations of the particle in an X-Y and Z direction. The method also includes generating control signals configured to drive the stage X-Y and Z position controls to track the movement of the particle.

The method may also include receiving current LSM scanning mirror positions and LSM detector readouts and synchronizing them with current stage position to generate an LSM pixel stamped with stage position and generating a 3D image showing the 3D trajectory of a particle using the LSM pixel stamped with stage position. The method may also include receiving current LSM scanning mirror positions and LSM detector readouts and synchronizing them with current stage position to generate an LSM pixel stamped with stage position. The method may also include converting each detector readout (pixel) from the LSM system from lab frame to a three dimensional voxel in a sample frame based on known magnification of the LSM system (real space pixel size), and the piezoelectric stage position at each time point during the scan of the sample. The method may also include generating interpolated data including average oversampled voxels and interpolated unsampled voxels. The method may also include smoothing the interpolated data. The method may also include generating a 3D image showing movement of the particle based on the interpolated data.

The tracking excitation laser beam may be oriented parallel to an optical table plane and X-Y radiation gathering components are mounted vertically with respect to the optical table plane. Each X-Y radiation gathering component may have a mirror configured to reflect light from the plane of the optical table to a vertical orientation. The method may also include providing a vertical mounting surface having X radiation gathering components mounted to one side and Y radiation gathering components mounted to an opposite side.

DETAILED DESCRIPTION

Multiscale Spectral Nanoscopy (MSN)

This disclosure is directed to Multiscale Spectral Nanoscopy (MSN), 3D single-particle tracking spectroscopy enabled by Single Nanoparticle Tracking Spectroscopic Microscope (SNTSM). This technique allows extremely high spatial and temporal resolution. Importantly, the time-dependent spectroscopic capability affords the study of molecule-level structural changes (the quantum-mechanical region), pushing the spatial information down to sub-nm scale. The MSN system adds the large scale contextual information of a laser scanning microscope (LSM) such as a the 2-photon LSM or confocal LSM to the temporal and spatial resolution of the SNTSM, creating an ideal system for addressing experiment where multiple scales are involved. It should be understood that either type of LSM is suitable for use in connection with the disclosure herein.

In general, MSN combines the high spatial and temporal resolution imparted by the original SNTSM design, with the larger-scale contextual information provided by an LSM, e.g., a 2-photon scanning fluorescence microscope. This is the first microscope system capable of covering length scales from the particle tracking super resolution (~10 nm) up to multicellular scales that can be achieved with 2-photon scanning fluorescence microscopy, as well as time scales ranging from microseconds to minutes and hours—truly multiscale capabilities.

The original SNTSM system made it possible to perform real-time three-dimensional single nanoparticle tracking through the use of a fast 3D piezo stage and a light feedback loop which moves the entire sample to counteract the movement of the nanoparticle. This results in the nanoparticle being effectively "held" in the focus of the microscope objective lens, despite the fact that the nanoparticle is still free to probe its local environment. This original implementation came with high spatial (~10 nm) and temporal (down to 10 μs) resolution. In addition the high spatiotemporal resolution, the most important facet of the SNTSM system is the ability to perform highly sensitive spectroscopic techniques on the nanoparticle probe, due to the fact that the nanoparticle is held in the focus of the objective at all times. This allows the user to probe the properties of a single moving nanoparticle or its environment, and has already been used to probe the spectral properties of single gold nanoparticles freely diffusing in solution.

Despite its many strengths, the SNTSM system is unable to evaluate the larger-scale environment of the nanoparticle-tracking probe. The SNTSM is based on a modified confocal microscope which evaluates only the focal volume of the objective lens. This in turn allows the SNTSM system to use fast, single-point photodetectors to perform the feedback loop, rather than relying on the relatively slow charge-coupled display imaging devices. This speed comes at the expense of the large-scale contextual information, however. To overcome this lack of large-scale context, the MSN system combines the power of the SNTSM with a scanning 2-photon microscope. The SNTSM enables the acquisition of high-precision spatial, temporal and spectral data from the nanoparticle probe, while the 2-photon scanning microscope provides large-scale information about the environment. The use of 2-photon fluorescence allows the microscope to take highly resolved optical sections while the nanoparticle probe samples different depths within the sample. The MSN could also be implemented with a confocal LSM which also has optical sectioning capabilities.

The MSN is a system that is well suited for use in biological systems. Biological problems are inherently multiscale, ranging from motions of proteins and their biochemical reactions at the nanometer scale to motions of organelles at the submicron scale to cell-cell signaling at the 100 μm scale. The MSN system is able to simultaneously observe all these phenomena. Simultaneously, the MSN system carries the spectroscopic power of the original SNTSM design, allowing the user to use state of the art single molecule spectroscopies to probe down to length scales where quantum mechanical effects dominate (~1 Å).

Figure 1:
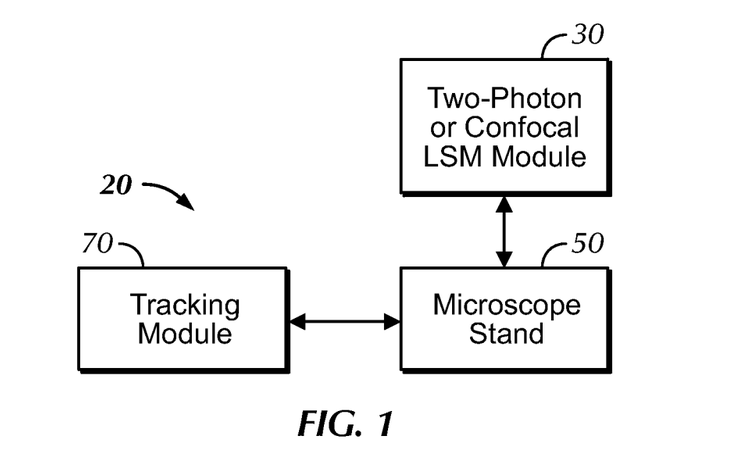
FIG. 1 is a block diagram of an MSN system.

FIG. 1 is a basic block diagram of an MSN system 20. In this example, the system generally includes a 2-photon or confocal laser scanning microscope (LSM) 30 interconnected with a microscope stand 50 and a tracking module 70. An important principle implemented in combining the power of an LSM with the SNTSM system is spectral separation of the signals from each system. The particle tracking module must not be influenced by the scanning 2-photon beam or any fluorescence generated by the environment. The single particle tracking may be performed in the near infrared (NIR), from 600-750 nm, where cellular autofluorescence is minimized. In one embodiment, the 2-photon LSM uses a femtosecond pulsed laser (e.g., Tsunmai, Newport) operating between 800 and 1000 nm coupled to a commercial LSM system (e.g., Zeiss LSM 410). When configured for confocal LSM, a continuous wave (CW) laser excitation can be used.

Figure 2:
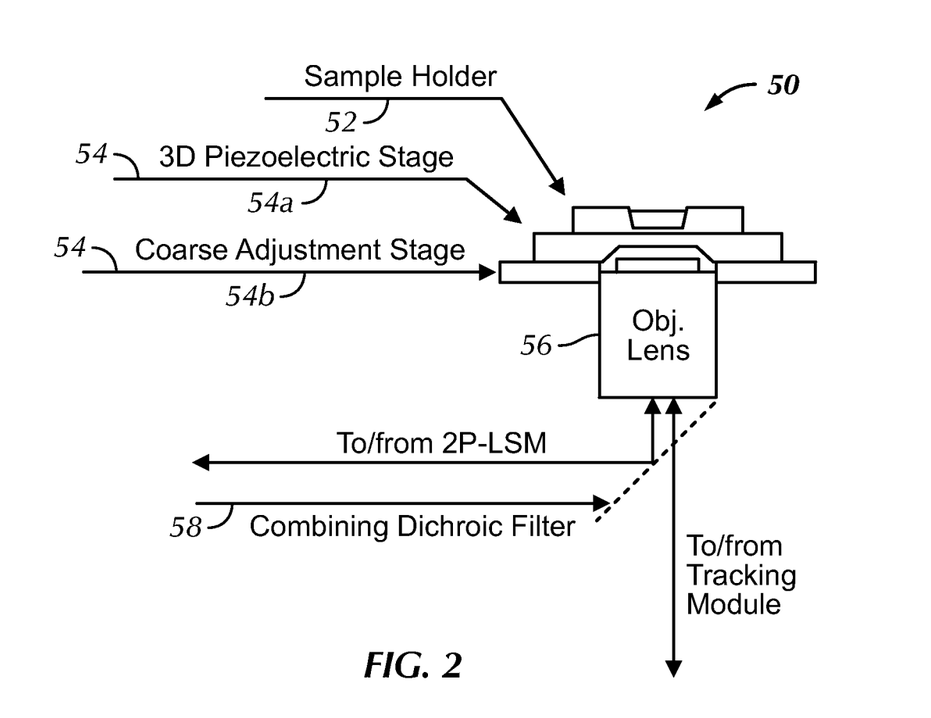
FIG. 2 is a block diagram of a microscope stand configured for use with an MSN system.

FIG. 2 is a block diagram of a microscope stand 50 configured for use with an MSN system. The microscope stand 50 includes a sample holder 52 (i.e., a particle-holding device with a particle coupled to the particle-holding device) and a stage 54 configured to provide X-Y and Z position control. In this example, the stage 54 includes a 3D piezoelectric stage 54a and a coarse adjustment stage 54b. It should be understood that other stage configurations are suitable for use with the configurations disclosed herein. For example, a suitable stage for use with the MSN system may have a volume size of 75×75×50 μm3 at 0.1 nm resolution. The stage 54 is configured to move the sample holder (and sample or particle) relative to the objective lens 56. In one example, the objective lens is a Zeiss 100× PlanApo although a wide range of objective lenses are suitable for use with the configurations disclosed herein. The microscope stand 50 also includes a combining dichroic filter 58 configured to fully reflect the 2-photon excitation and emission (400-600 nm) to/from 2P-LSM 30 and also transmit all light related to the tracking module to the tracking module 70. It should be understood that the choice of combining dichroic filter is determined by the chosen wavelengths for tracking and LSM and can vary depending on the application.

Figure 3A:
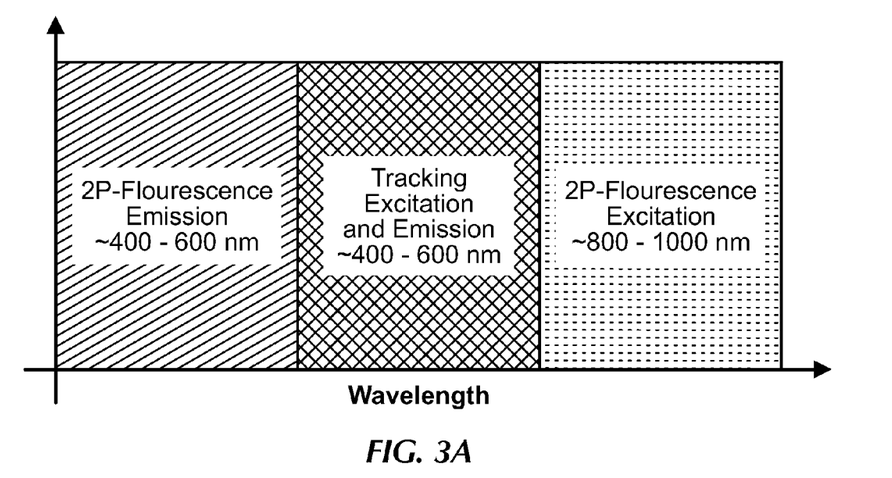
FIG. 3*a* is a graph showing an example of the excitation and emission wavelengths of an example MSN system.

FIG. 3a is a graph showing an example of the excitation and emission wavelengths of an example MSN system. As noted above, single particle tracking may be performed in the near infrared (NIR), from 600-750 nm, where cellular autofluorescence is minimized. In one embodiment, the 2-photon LSM uses a femtosecond pulsed laser (e.g., Tsunmai, Newport) operating between 800 and 1000 nm coupled to a commercial LSM system (e.g., Zeiss LSM 410). As noted above, a number of wavelength combinations is possible with the requirement that the LSM and tracking excitation and emission do not overlap.

Figure 3B:
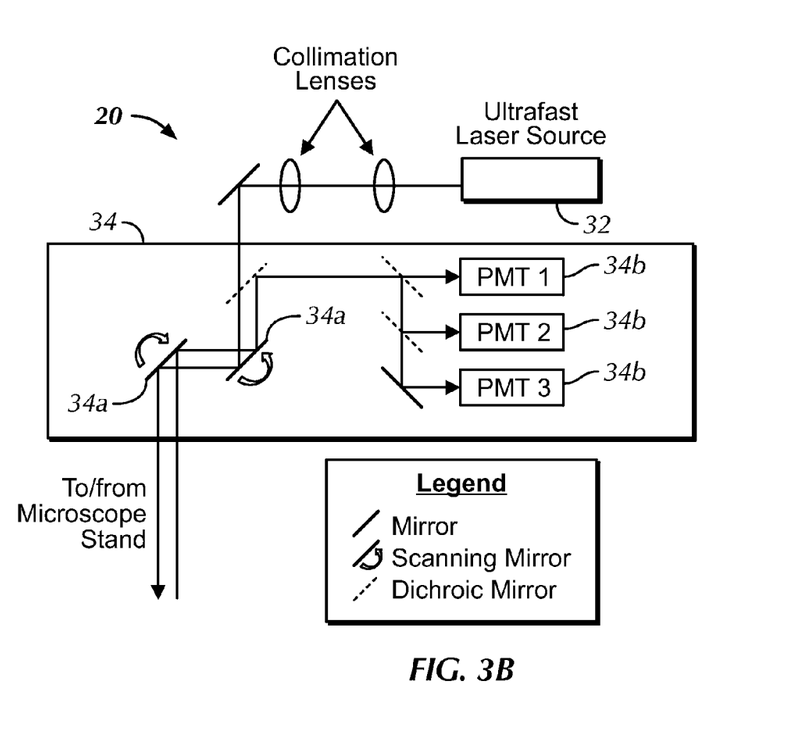
FIG. 3*b* is a block diagram of a 2P-LSM.

FIG. 3b is a block diagram of a 2P-LSM 30. The 2P-LSM 30 generally includes an ultrafast pulsed laser source (e.g., Newport Tsunami) tuned to the desired frequency (e.g., 900 nm) coupled to a laser scanning microscope 34 (e.g., Zeiss LSM 410, LSM Tech). The scanning mirrors 34a inside the LSM unit raster scan the pulsed laser across the sample through a 100× objective (e.g., Zeiss). The collected two photon excited fluorescence is descanned through the same set of mirrors and focused onto three photomultiplier tube (PMT) detectors 34b, which can read out simultaneous signals from multiple spectral windows. In general, the LSM module can be implemented with any number of detection channels depending on the desired experiment.

Figure 4:
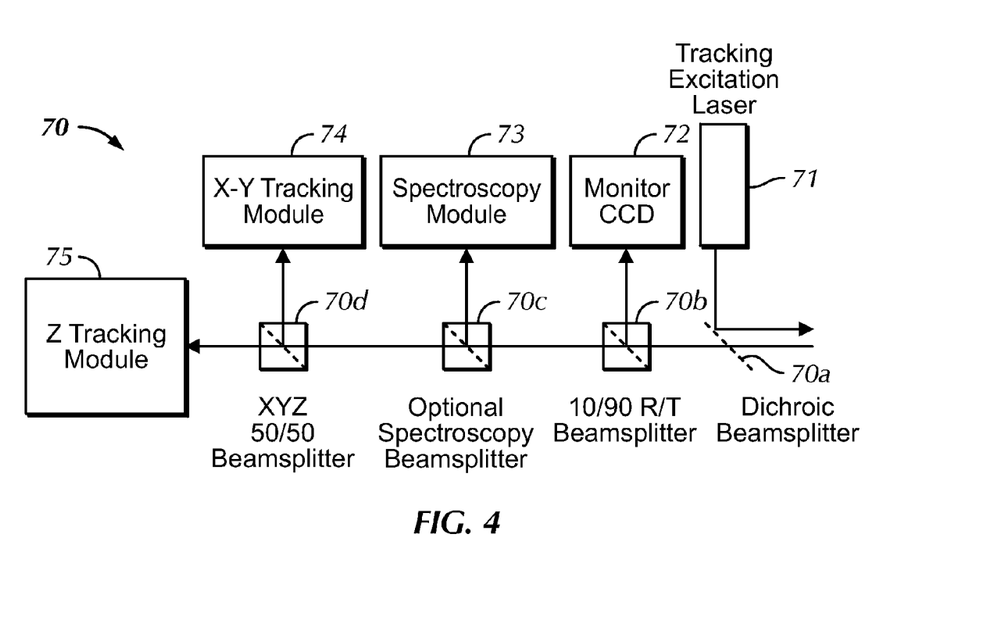
FIG. 4 is a block diagram of a tracking module.

FIG. 4 is a block diagram of a tracking module 70. The tracking module 70 generally includes a tracking excitation laser 71, monitor CCD 72, spectroscopy module 73, X-Y tracking module 74 and a Z tracking module 75 all coupled to the light path from the 2P-LSM 30 via beamsplitters 70a-70d as shown in FIG. 4. The optics for the tracking module may be coupled into the side entrance port of the 2P-LSM 30, with the tube lens removed allowing access to the infinity path of the objective. In one example, the tracking excitation laser is a 642 nm diode (Coherent Cube), which is separated from the tracking emission by a 655 nm longpass dichroic 71a. The particle emission is sent to the tracking optics, which are derived from the original SNTSM design. This implementation is modified to reduce the overall footprint of the tracking system to a 3'×1.5' area.

Figure 5:
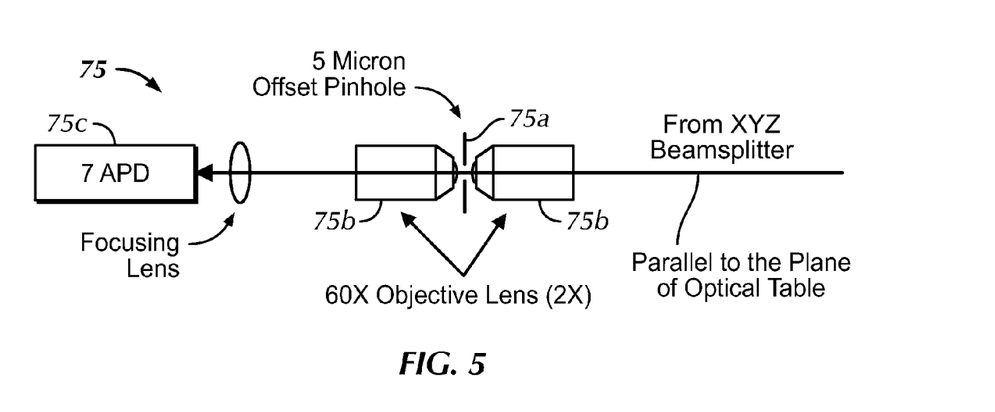
FIG. 5 is a block diagram of a Z tracking module.

FIG. 5 is a block diagram of a Z tracking module 75. Particle deviations in the Z (optical axis) direction are monitored using a slightly offset pinhole 75a imaged via two objective lenses 75b (e.g., 60x objective lens) onto an avalanche photodiode (APD) 75c which gives a nearly linear index into the deviation in Z. The Z APD output may be normalized against the four X-Y APDs discussed below.

Figure 6:
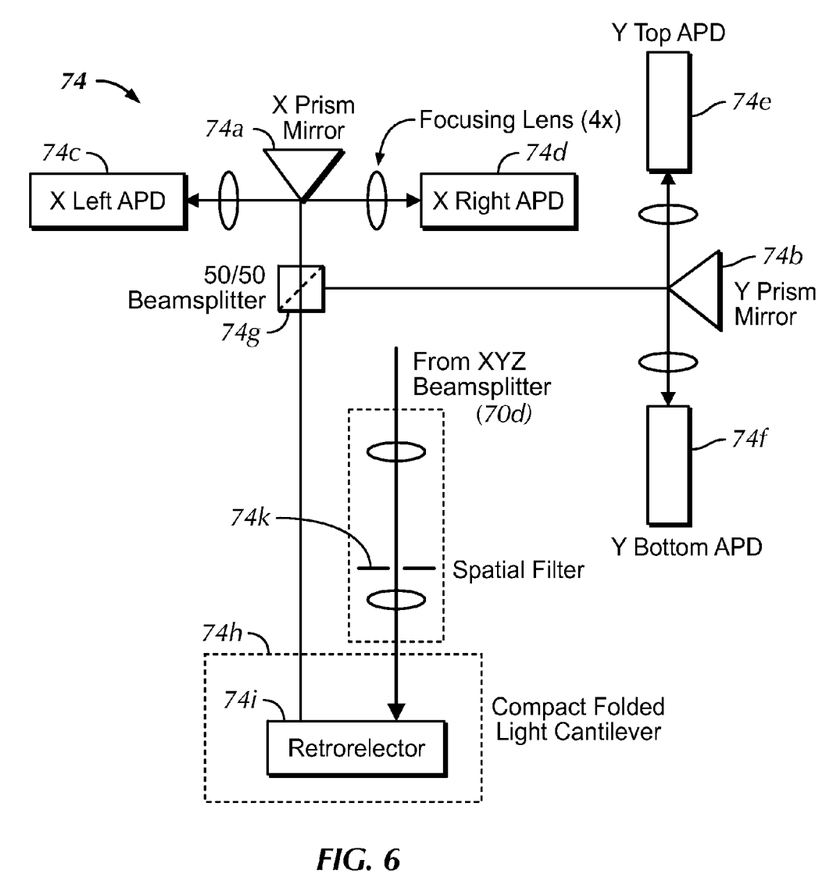
FIG. 6 is a block diagram of the X-Y tracking module.

FIG. 6 is a block diagram of the X-Y tracking module 74. To detect particle deviations in the X and Y directions, the emission spot is split by beamsplitter 74g and projected onto two orthogonal prism mirrors, X prism mirror 74a and Y prism mirror 74b. The X prism mirror 74a splits the split the signal onto two single photon counting avalanche photo-diodes (APD), left APD 74c and right APD 74d. The Y prism mirror 74b splits the split the signal onto top APD 74e and bottom APD 74f. Suitable APD are available from a variety of manufacturers including Perkin Elmer.

A variety of focusing lenses may be used as shown in FIG. 6. The output from the XYZ beamsplitter 70d (FIG. 4) is directed to a compact folded light cantilever 74h including a retroreflector 74i to provide the signal for beamsplitter 74g. The output from the XYZ beamsplitter 70d may also be directed through a spatial filter 74k and various focusing lenses.

When the particle is centered with respect to the X or Y axis, the left and right or top and bottom APDs have an equal reading. As the particle deviates from this center position, one of the APDs will show an increased signal relative to the other and this difference (normalized by the sum of the intensity on both detectors) is used as an error readout for the feedback control.

Figure 10:
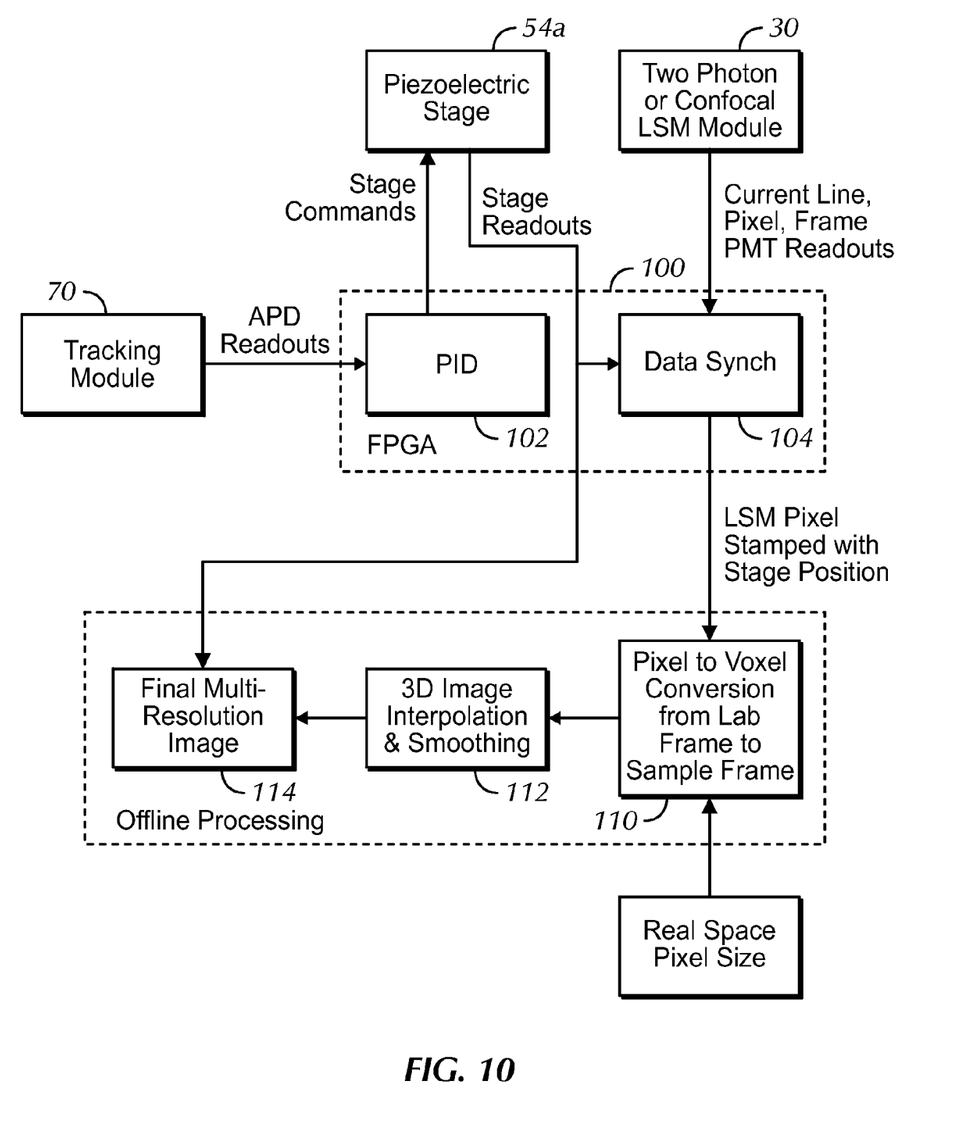
FIG. 10 is a block diagram showing the data flow for an MSN system.

In one embodiment, the signals from the X, Y and Z tracking APDs are fed into a field programmable gate array (e.g., FPGA, NI PCIe-7852R, National Instruments) as shown in FIG. 10, where the APD counts are filtered and converted to control signals using a proportional, integration and differentiation (PID) algorithm. These controls are output by the FPGA as analog voltages which are sent to the 3D piezo stage to complete the feedback loop. The loop may be run at 100 kHz (10 μsec) so that fast motions can be tracked and compensated by the stage. In one embodiment, the localization precision of a stationary particle is ~10 nm in X and ~13 nm in Y and Z. The coregistration of the tracking and 2P-LSM data may be performed on the FPGA. A breakout cable on the 2P-LSM 30 may allow for direct measurement of the pixel clock and photomultiplier tube (PMT) voltages, which are then correlated with the stage position at the readout time of each voxel, allowing each voxel to be converted from the lab frame to the sample frame.

Figure 7:
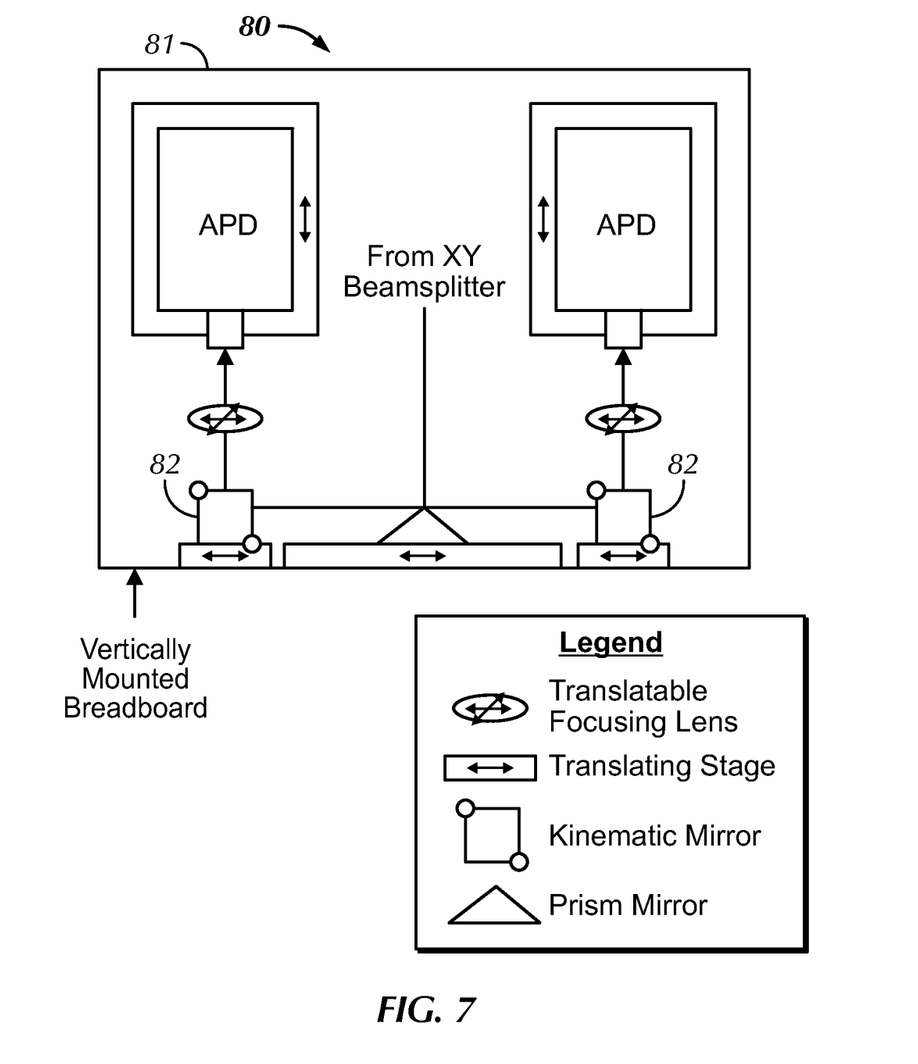
FIG. 7 is a block diagram of a X-Y compact vertical APD mounting (Front View)
Figure 8:
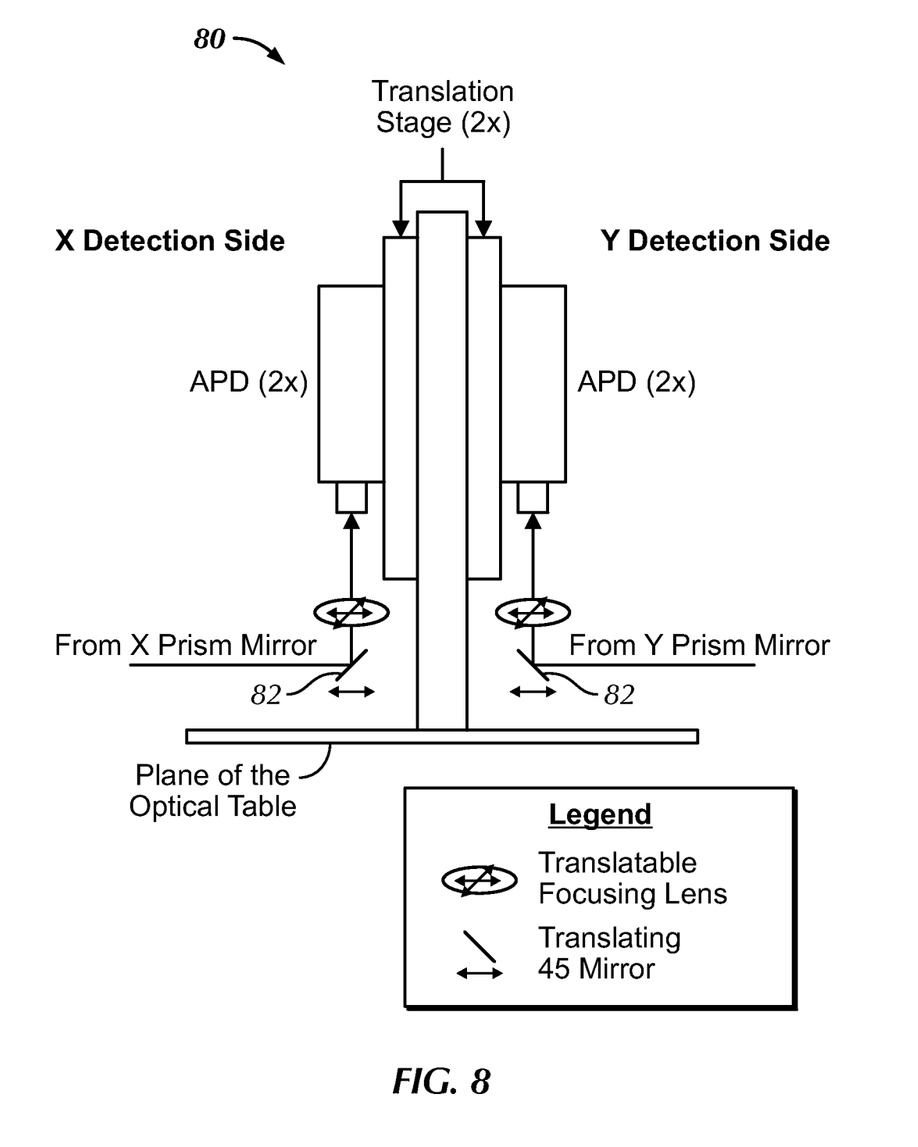
FIG. 8 is a block diagram of a X-Y compact vertical APD mounting (SideView)
Figure 9A:
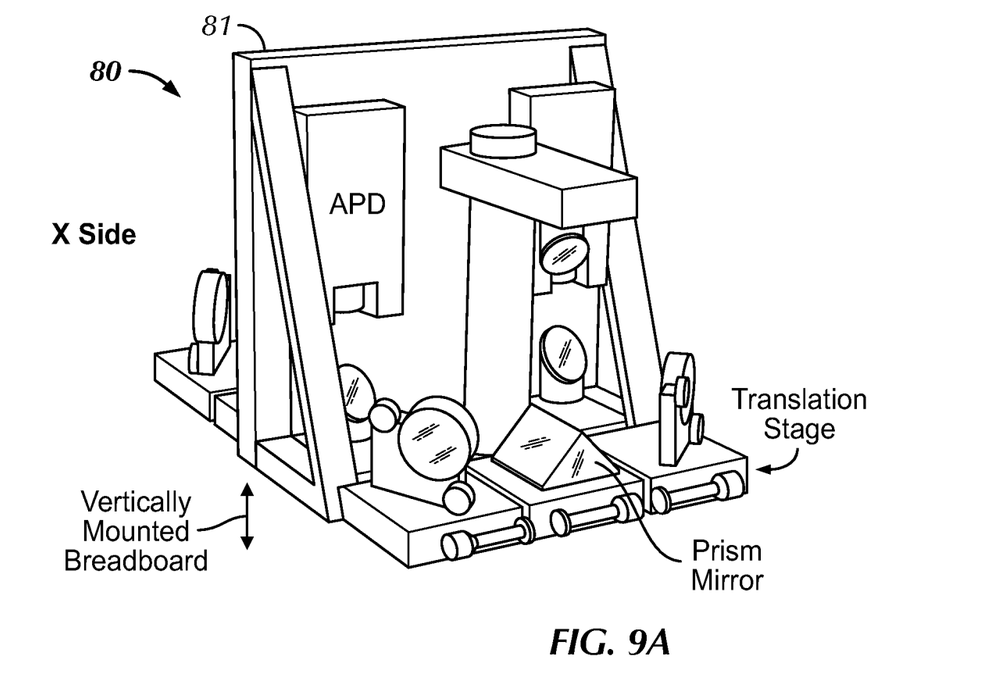
FIGS. 9*a* and 9*b* are diagrams showing a compact 3D architecture for X-Y tracking detection.
Figure 9B:
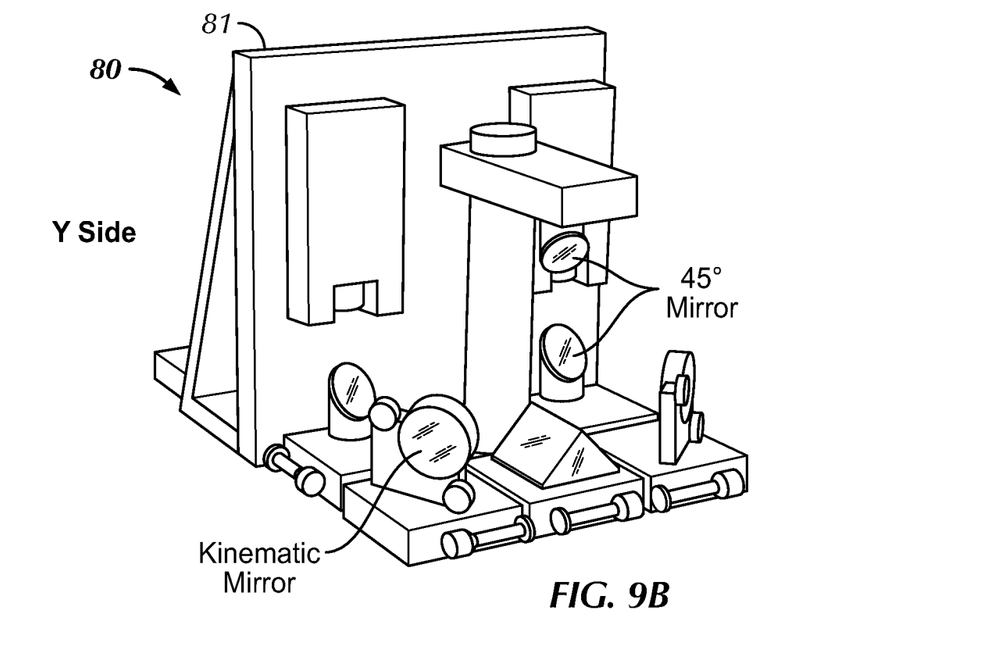

FIG. 7 is a block diagram showing a front view of a X-Y compact vertical APD mounting 80. The term vertical as used herein refers to a 90° orientation with respect to the plane of the optical table. In a traditional embodiment such as the schematic block diagram in FIG. 6, all of the X-Y APDS are oriented parallel to the plane of the optical table. In this embodiment, the four avalanche photodiodes (APDs) required for X-Y tracking are vertically mounted either side of a vertical breadboard 81 to save as much space as possible and provide ease of alignment. Each APD has an associated mirror 82 configured to reflect light from the plane of the optical table to a vertical orientation. Spectroscopy is performed by splitting of the light from the tracking module using a beamsplitter and directing it to pair of APDs separated by a dichroic, or by using a spectrometer. In this example an 8/92 reflection/transmission pellicle beamsplitter is used to split a small portion of the tracking signal to a camera for monitoring the particle during tracking (Cascade 512b, Photometrics). It should be understood that in FIG. 7 only 2 of the 4 X-Y APDs are shown. Each APD has an associated translatable a focusing lens that focuses light though a kinematic mirror. The kinematic mirrors and a prism mirror each have associated translating stages. FIG. 8 is a block diagram showing a side view of the X-Y compact vertical APD mounting 80. FIGS. 9a and 9b are diagrams showing a compact 3D architecture for the APD mounting 80.

FIG. 10 is a block diagram showing the data flow for an MSN system. The tracking module 70 detects deviations in the particle's X, Y and Z positions using the tracking module APDs. The tracking module APD outputs are coupled to a processor 100. In this example, the processor is implemented as an FPGA. The FPGA or processor converts the detector signals from the tracking module to error functions which describe the deviation in the particle's position from the objective's focus. The error signals are processed using a proportional, integration and differentiation (PID) approach shown generally by block 102. These control signals are output by the FPGA as analog voltages which are sent to the stage 54a to complete the feedback loop. The stage 54a moves the sample to counteract the particle's motion and minimize the error functions. It should be understood that feedback generation circuitry can be implemented in a variety of ways including an analog circuit, a digital signal processor, a field-programmable-gate-array (FPGA), or software running on a computer or microcontroller. The loop may be run at 100 kHz (10 μsec) so that fast motions can be tracked and compensated by the stage. In one embodiment, the localization precision of a stationary particle is ~10 nm in X and ~13 nm in Y and Z.

While the particle is held in the objective's focus, the two-photon or confocal laser scanning microscope 30 scans the current optical section. As the LSM excitation beam moves through the sample (e.g. fluorescently stained cells), the sample is also being moved by the tracking system and the image collected by the two-photon or confocal LSM will be corrupted by the motion of the sample. To extract the true local three dimensional image, the current position of the LSM scanning mirrors (i.e. the line and pixel positions within an LSM optical section) and the LSM detector readouts are sent to the FPGA or processor unit, where they are synchronized with the current stage position as shown generally by block 104. This is achieved by making a data set which contains each pixel readout from the LSM, including pixel, line and frame values, detector reading and the piezoelectric stage readouts. This is done onboard the FPGA or processor and all subsequent processing is done in post-processing, which in this implementation is performed in MATLAB.

Using the scan mirror positions, known magnification of the two photon or confocal LSM system (real space pixel size), and the piezoelectric stage position at each timepoint during the experiment, each detector readout (pixel) from the LSM system is converted from the lab frame, where the sample is moving and the particle is stationary, to a three dimensional voxel in the sample frame, where the sample is now stationary as shown by block 110. To achieve this, the spot where the particle is held by the tracking module is referenced to a particular line and pixel value on the LSM. In this implementation, the tracking and LSM units were aligned such that the particle was held at the middle of the LSM image. In this example, the images collected had 512 pixels and 512 lines (though any combination is possible) and the tracking spot was located at pixel 256 and line 256. This is then used as the reference point with which to measure the position of the LSM scanner and the tracked particle at any given point. At a given pixel P and line L, the position is offset by the reference point (here pixel 256, line 256). The distance in pixel/line is then converted to a real distance using the known size the pixel in the LSM system, which is determined by the choice of optics. In this implementation, the pixels size is 83.1 nm, but can take on a range of values. Using this value we convert the pixel and line values to real space X and Y values for each LSM reading. The Z value is determined by the current Z reading on the piezo stage. This gives a set of 3D voxels which describe the 3D environment around the tracked particle.

Figure 11:
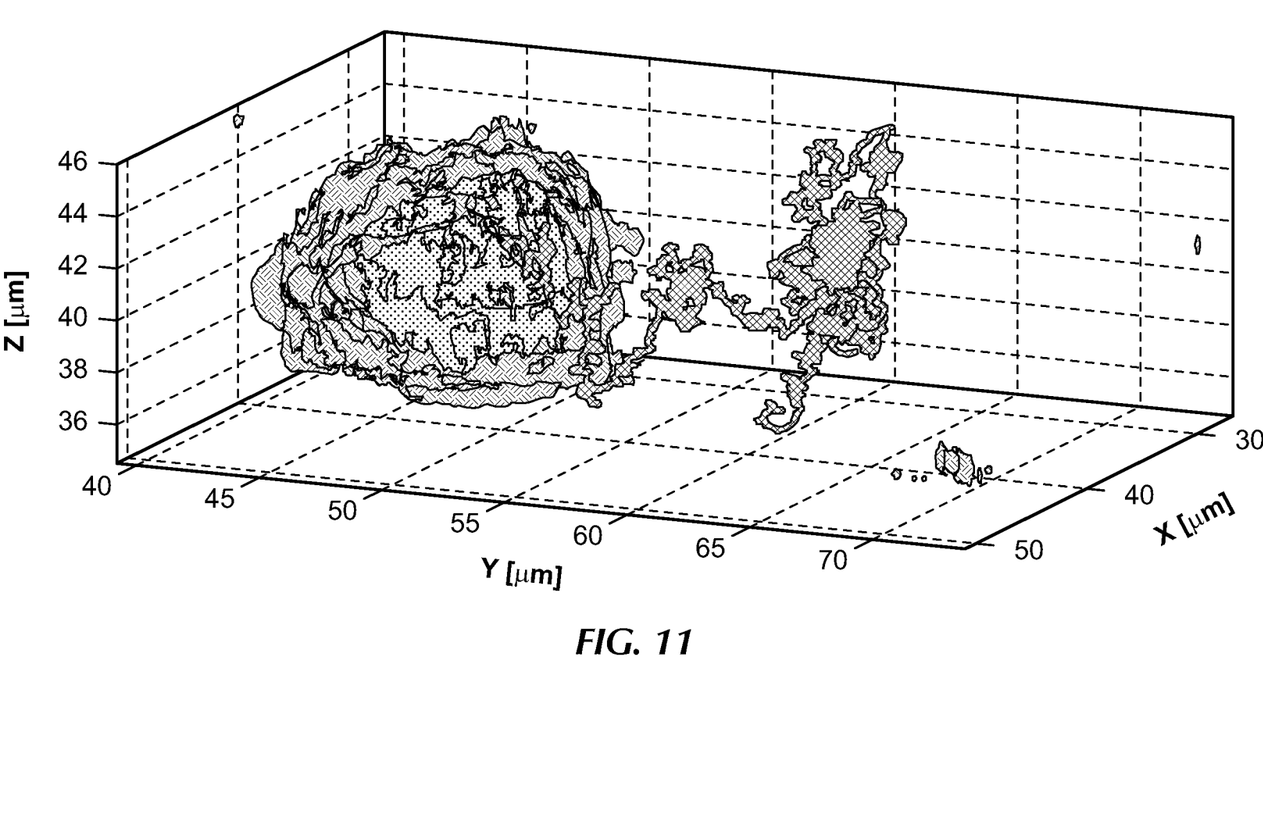
FIG. 11 is a 3D image showing the 3D trajectory of a particle.

This set of 3D voxels will be unevenly sampled, as the particle randomly passes through different areas of the sample. As a result, voxels may be sampled multiples times while others remain unsampled. To create a 3D image, these oversampled voxels are averaged, while interpolation algorithms are used to estimate values for unsampled voxels. From here, the 3D image can be subject to common image processing techniques, such as smoothing as generally shown by block 112. This 3D image can be combined with the trajectory of the particle during the trajectory (observed via the piezoelectric stage readouts) to create a 3D multi-scale, multiresolution data set. The small scale, high resolution (~10 nm, ~10 µsec) data of the particle's trajectory is complemented with large scale, lower resolution information of the 3D image, which may be up to ~100 microns depending on choice of magnification for the LSM system. FIG. 11 is a 3D image showing the 3D trajectory of a particle as discussed above. In this example, the image shows a freely diffusing 93 nm near infrared fluorescent nanoparticle which lands on a macrophage cell.

In this example, the generation of a 3D image is shown using an offline processing module 106. It should be understood that a variety implementations may be used to generate the 3D image based in the data generated by the synchronization module 104, including a digital signal processor, a field-programmable-gate-array (FPGA), or software running on a computer or micro-controller.

In one embodiment, the interface for all instruments is performed in LabVIEW. The control implements a Kalman filter, PID control and synching with confocal data. The confocal data is achieved by directly reading the voltage of the PMTs inside the LSM. The data is then adjusted offline to compensate for the effect of the stage movement on the pixel location.

For the tracking module, important limitations are the speed of the piezo stage and the photostability of the fluorescent probe. The state of the current piezo technology limits tracking to 60 nm nanoparticle in a pure water solution. This is simply a function of the time it takes the stage to respond to the signal from the tracking system, rather than a lack of photons. The previous SNTSM system showed that a single quantum dot provides enough photons to be tracked in viscous media. This hurdle is lessened in biological systems, where the crowded nature of the intracellular environment slows diffusion significantly.

The photostability and lifetime of the fluorescent probe also limits the instrument. Due to the constant illumination of the tracking probe, a robust emitter is required, precluding the use of organic fluorophores or fluorescent proteins. Quantum dots are extremely robust, but display intermittency in their emission, making tracking difficult. This problem can be solved through the use of probes composed of multiple quantum dots to enhance the probability that one will be emitting at all times. Also, recent research has shown that intermittency can be alleviated or eliminated through careful control of the quantum dot structure.

The MSN system may be implemented as a commercial grade microscope for research groups and companies with biological specialties. The system may be packaged wholesale as an all-in-one system or the tracking module may be sold as an add-on to any confocal microscope system, which many biology groups already possess. The smaller footprint of the new tracking module allows for easier implementation. The existing confocal microscope would only need to add a piezo stage and have access to the infinity path of the objective to add on the tracking module and make a fully functioning MSN system. It should be understood that the MSN system may be used in a variety of applications including but not limited to those listed herein.

Elucidation of Cellular Dynamics:

Due to its unique combination of high spatial and temporal resolution with large spatial scale, the MSN system is uniquely suited to study the dynamic behavior of organelle trafficking along the microtubule-based cytoskeletal network. Microtubules are the subcellular structures which allow for transport of organelles within the cell and also play a fundamental role in cell division. However, the study of microtubule-based transports in vivo has been difficult, with organelles traveling along their three-dimensional helical structure at speeds of 1-2 µm/sec. The MSN system will be able track this fast 3D motion of organelles in real time given that the microtubule diameter (25 nm) is well within the spatial resolution of our system (~10 nm). Moreover, by fluorescently labeling the tubulin subunits and taking advantage of MSNs ability to evaluate the large-scale environment, we will be able to visualize the entire process in its full 3D context. The MSN prototype has already been able to detect the motion of nanoparticles within living cells.

Environmental Sensing Through High-Resolution Spectroscopy:

A major strength of the MSN system is its ability to effectively keep the particle of interest in the focal volume of the objective lens at all times. The particle itself can still freely move within the sample while the experimenter has the ability to probe the particle and its environment as if it were stationary in the lab frame. This allows high-precision, time-dependent spectroscopy to be performed within the focal volume, despite the 3D motion of the nanoparticle. The MSN system can track and monitor semiconductor quantum dots which can be engineered to be sensitive to pH, temperature, as well as a wide variety of chemicals and biological macromolecules. By analyzing the spectral readout of the quantum dot sensor, the MSN system can be applied to hitherto unexplored areas of cell biology, such as subcellular temperature, pH and electric field. Importantly, the MSN system will provide spectral readouts with high spatial and temporal resolution, which is essential for sensing the local dynamic heterogeneities in the biological environment and its functional consequence. For example, temperature sensitive quantum dots can be passivated with mitochondrial targeting peptides, allowing highly localized temperature measurements at the mitochondria and at control areas in the cytosol to record the intracellular temperature gradient. The cell can then be chemically stimulated to see how the local temperature gradient depends on the state of the cell. Finally, the addition of chemical agents to uncouple oxidative phosphorylation, such as carbonyl cyanide p-(trifluoromethoxy) phenyl hydrazone (FCCP), can help determine if the local temperature depends on the inefficiencies of cellular metabolism. The direct measurement of mitochondrial temperature could have a far-reaching impact on cancer biology and neurobiology.

In Vivo Single-Molecule Dynamics:

To elucidate the manner by which molecular conformations and reactivity of proteins impact on organelle- or cellular-level functions, merely tracking the spatial location is not sufficient. To follow the intra-molecular dynamics, which occur on a length scale where quantum mechanics must be considered, the MSN system can employ sensitive spectroscopic methods such as Förster-type Resonance Energy Transfer (FRET) spectroscopy, a molecular scale ruler which has enabled researchers to observe protein structure and dynamics by measuring the relative intensities of donor and acceptor fluorophores to extract the distance between two amino acid residues. Time-dependent FRET trajectories yield information on the dynamics of proteins, such as folding/unfolding and conformational changes in the presence of substrate, even at the single-protein level (called single-molecule FRET or smFRET). The study of proteins at the single-molecule level has the ability to elucidate molecular states that cannot be observed via traditional ensemble measurements, where the observable is typically the population mean. However, this kind of high-resolution single-molecule measurement has not been achieved in vivo due to the inability to track and observe a protein in the 3D cellular environment. Applying the MSN system to the intracellular environment represents a complete paradigm shift in how single-molecule measurements are done in biological systems. By attaching a single FRET labeled protein to the tracked nanoparticle, single-molecule FRET measurements can be performed to observe protein dynamics in a myriad of biological environments, from freely diffusing outside the cell to floating on lipid rafts in the cellular membrane to inside the cell where the protein can function in its native state. Capturing transient protein-protein interactions is but one of the many experiments that cannot be done otherwise. Moreover, these single-molecule measurements can be placed in the larger context of the cell or multicellular organism using the 2-photon fluorescence scanner of the MSN system.

Affecting Change in the Cellular Environment:

The MSN can also be used to affect the highly localized changes in the cellular environment. Attaching a metal nanoparticle can allow local heating to activate of thermally sensitive pathways or enable nanoscale photothermal therapy. Photoactivated uncaging or photocleavable linkers can be used to deliver small molecules, peptides, RNAs and proteins to cell with high precision. Delivery of these cargoes will be achieved breaking the photocleavable bond with a pulse of UV light once the nanoparticle has arrived at a desired location within the biological system.

The references listed herein are also part of the application and are incorporated by reference in their entirety as if fully set forth herein. It should be understood that many variations are possible based on the disclosure herein. Although features and elements are described above in particular combinations, each feature or element can be used alone without the other features and elements or in various combinations with or without other features and elements. The methods or flow charts provided herein may be implemented in a computer program, software, or firmware incorporated in a non-transitory computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs)

What is claimed is:

1. A system for non-invasively tracking a particle in a sample, comprising:
    a 2-photon or confocal laser scanning microscope (LSM) configured to scan the sample, comprising:
        a plurality of scanning mirrors; and
        a plurality of detectors;
    a particle-holding device with the particle coupled to the particle-holding device, the particle-holding device being coupled to a stage with X-Y and Z position control;
    a tracking module comprising:
        a tracking excitation laser,
        X-Y radiation-gathering components configured to detect deviations of the particle in an X-Y direction,
        Z radiation-gathering components configured to detect deviations of the particle in a Z direction, and
        a processor, coupled to the X-Y and Z radiation gathering components, configured to generate control signals to drive the stage X-Y and Z position controls to track movement of the particle; and
    a synchronization module configured to synchronize the LSM and tracking module by:
        receiving current scanning mirror positions and detector readouts from the LSM;
        receiving a current stage position from the tracking module; and
        generating an LSM pixel stamped with a stage position.

2. The system of claim 1 further comprising a processing module configured to generate a 3D image showing the 3D trajectory of a particle using the LSM pixel stamped with the stage position.

3. The system of claim 2 further comprising a pixel to voxel conversion module configured to convert each detector readout from a lab frame to a three dimensional voxel in a sample frame based on known magnification of the LSM system and a piezoelectric stage position at each time point during the scan of the sample.

4. The system of claim 3 further comprising an interpolation module configured to generate interpolated data including average oversampled voxels and interpolated unsampled voxels.

5. The system of claim 4 further comprising a smoothing module configured to smooth the interpolated data.

6. The system of claim 4 further comprising an image generating module configured to generate a 3D image showing movement of the particle based on the interpolated data.

7. The system of claim 1 wherein the tracking excitation laser is mounted parallel to an optical table plane and the X-Y radiation gathering components are mounted vertically with respect to the optical table plane.

8. The system of claim 7 wherein each X-Y radiation gathering component has a mirror configured to reflect light from the plane of the optical table to a vertical orientation.

9. The system of claim 7 further comprising a vertical mounting surface having X radiation gathering components mounted to one side and Y radiation gathering components mounted to an opposite side.

10. A method for non-invasively tracking a particle in a sample, comprising:
    providing a 2-photon or confocal laser scanning microscope (LSM) with a plurality of scanning mirrors and a plurality of detectors configured to scan the sample;

providing a particle-holding device with the particle coupled to the particle-holding device, the particle-holding device being coupled to a stage with X-Y and Z position control;

providing a tracking module configured to:
 generate a tracking excitation laser beam;
 detect deviations of the particle in an X-Y and Z direction; and
 generate control signals to drive the stage X-Y and Z position controls to track movement of the particle; and synchronizing the LSM and tracking module by:
 receiving current scanning mirror positions and detector readouts from the LSM;
 receiving a current stage position from the tracking module; and
 generating an LSM pixel stamped with a stage position.

11. The method of claim 10 further comprising generating a 3D image showing the 3D trajectory of a particle using the LSM pixel stamped with the stage position.

12. The method of claim 11 further comprising converting each detector readout from a lab frame to a three dimensional voxel in a sample frame based on known magnification of the LSM system and a piezoelectric stage position at each time point during the scan of the sample.

13. The method of claim 12 further comprising generating interpolated data including average oversampled voxels and interpolated unsampled voxels.

14. The method of claim 13 further comprising smoothing the interpolated data.

15. The method of claim 13 further comprising generating a 3D image showing movement of the particle based on the interpolated data.

16. The method of claim 10 wherein the tracking excitation laser beam is oriented parallel to an optical table plane and X-Y radiation gathering components are mounted vertically with respect to the optical table plane.

17. The method of claim 16 wherein each X-Y radiation gathering component has a mirror configured to reflect light from the plane of the optical table to a vertical orientation.

18. The method of claim 16 further comprising providing a vertical mounting surface having X radiation gathering components mounted to one side and Y radiation gathering components mounted to an opposite side.

19. A system for non-invasively tracking a particle in a sample, comprising:
 an imaging module configured to scan the sample comprising:
  a laser scanning microscope (LSM);
  a plurality of scanning mirrors; and
  a plurality of single point detectors;
 a microscope stand comprising:
  a sample holder containing the sample; and
  a stage configured to provide X-Y and Z position control;
 a tracking module comprising:
  a tracking excitation laser;
  X-Y radiation-gathering components configured to detect deviations of the particle in an X-Y direction;
  Z radiation-gathering components configured to detect deviations of the particle in a Z direction; and
  a processor configured to generate control signals to drive the stage X-Y and Z position controls to track movement of the particle; and
 a synchronization module configured to synchronize the imaging module and tracking module by:
  receiving current scanning mirror positions and detector readouts from the imaging module;
  receiving a current stage position from the tracking module; and
  generating an LSM pixel stamped with a stage position.

* * * * *